(12) United States Patent
Yeh et al.

(10) Patent No.: US 8,123,959 B2
(45) Date of Patent: Feb. 28, 2012

(54) TREATMENT OF SOLID PARTICLES WITH FUNCTIONAL AGENTS

(75) Inventors: Eshan B. Yeh, Hartford, CT (US); Keith D. Solomon, Cheshire, CT (US)

(73) Assignee: 3M Innovative Properties Company, St. Paul, MN (US)

( * ) Notice: Subject to any disclaimer, the term of this patent is extended or adjusted under 35 U.S.C. 154(b) by 140 days.

(21) Appl. No.: 12/277,665

(22) Filed: Nov. 25, 2008

(65) Prior Publication Data

US 2009/0134099 A1   May 28, 2009

Related U.S. Application Data

(60) Provisional application No. 60/990,703, filed on Nov. 28, 2007, provisional application No. 60/990,688, filed on Nov. 28, 2007.

(51) Int. Cl.
*C02F 1/50* (2006.01)
*B05D 1/00* (2006.01)

(52) U.S. Cl. ........ 210/764; 210/501; 210/506; 427/220; 427/375; 427/384; 427/424

(58) Field of Classification Search .............. 210/764, 210/501, 502.1, 506; 427/207.1, 208.2, 212, 427/215, 220, 222, 372.2, 375, 384, 430.1, 427/443.2, 213, 424
See application file for complete search history.

(56) References Cited

U.S. PATENT DOCUMENTS

| | | | |
|---|---|---|---|
| 3,560,385 A | 2/1971 | Roth | |
| 4,540,489 A | 9/1985 | Barnard | |
| 4,981,591 A | 1/1991 | Ostreicher | |
| 5,013,459 A | 5/1991 | Gettings et al. | |
| 5,064,534 A | 11/1991 | Busch et al. | |
| 5,190,659 A | 3/1993 | Wang et al. | |
| 5,269,919 A | 12/1993 | von Medlin | |
| 5,882,517 A | 3/1999 | Chen et al. | |
| 5,985,308 A | 11/1999 | Burrell et al. | |
| 6,197,193 B1 | 3/2001 | Archer | |
| 6,375,969 B1 * | 4/2002 | Kostka et al. | 424/409 |
| 6,524,477 B1 | 2/2003 | Hughes | |
| 6,565,749 B1 | 5/2003 | Hou et al. | |
| 6,835,311 B2 | 12/2004 | Koslow | |
| 6,866,704 B2 | 3/2005 | Koslow | |
| 6,986,429 B2 | 1/2006 | Naji et al. | |
| 6,994,794 B2 | 2/2006 | Hansen et al. | |
| 7,112,272 B2 | 9/2006 | Hughes et al. | |
| 7,112,280 B2 | 9/2006 | Hughes et al. | |
| 2003/0047514 A1 | 3/2003 | Manzone | |
| 2004/0164018 A1 | 8/2004 | Mitchell et al. | |
| 2004/0168973 A1 | 9/2004 | Hughes et al. | |
| 2004/0182790 A1 | 9/2004 | Manzone | |
| 2004/0195180 A1 | 10/2004 | Cumberland et al. | |
| 2004/0206882 A1 | 10/2004 | Banks et al. | |
| 2005/0056582 A1 | 3/2005 | Patel et al. | |
| 2005/0126970 A1 | 6/2005 | Maeda | |
| 2005/0211635 A1 | 9/2005 | Yeh et al. | |
| 2005/0242041 A1 | 11/2005 | Cumberland | |
| 2005/0279696 A1 | 12/2005 | Balm et al. | |
| 2007/0022210 A1 | 1/2007 | Roy et al. | |
| 2007/0075025 A1 | 4/2007 | Patel et al. | |
| 2007/0221569 A1 | 9/2007 | Stouffer et al. | |

FOREIGN PATENT DOCUMENTS

| | | |
|---|---|---|
| JP | 2002/265621 | 9/2002 |
| WO | WO-03/076044 | 9/2003 |

OTHER PUBLICATIONS

Grapski, et al., "Synthesis and Characterization of Non-Leaching Biocidal Polyurethanes", *Biomaterials* 22, (2000), 2239-2246.
Kanazawa, et al., "Polymeric Phosphonium Salts as Novel Class of Cationic Biocides. X. Antibacterial Activity of Filters Incorporating Phosphonium Biocides", *Journal of Applied Polymer Science*, vol. 54, (1994), 1305-1310.

\* cited by examiner

*Primary Examiner* — Nam Nguyen
*Assistant Examiner* — Lucas Stelling

(57) ABSTRACT

Provided are methods of modifying solid particles with functional agents to provide anti-microbial media. The anti-microbial media comprise a surface-modified inorganic component which is a reaction product of an anti-microbial component and an inorganic component. Methods of making the media include agitating inorganic base material in a processing tank substantially simultaneously with spraying the anti-microbial component into the processing tank to form a coated base material. Methods of making the media also include maintaining a ratio of the anti-microbial component to the inorganic component such that the coated base material is below its compaction point. Methods of use are also provided.

9 Claims, No Drawings

TREATMENT OF SOLID PARTICLES WITH FUNCTIONAL AGENTS

RELATED APPLICATIONS

This application claims the benefit of U.S. Provisional Patent Application No. 60/990,703, filed on Nov. 28, 2007, and U.S. Provisional Patent Application No. 60/990,688, filed on Nov. 28, 2007 the disclosures of which are incorporated by reference herein in their entirety.

TECHNICAL FIELD

The present disclosure relates to fluid filtration media and methods of making them. Specifically, provided are methods of modifying solid particles, such as diatomaceous earth, to provide anti-microbial media.

BACKGROUND

Often in both consumer and industrial fluid filtration applications a fluid is filtered prior to its use in an intended application. As a result, fluid filtration systems are installed either internally or externally within the industrial system or consumer appliance.

The EPA Water Purifier Standard requires that a filtration device for drinking water applications remove microorganisms at greater than 6 log for bacteria, 4 log for virus and 3 log for protozoan cysts ("Guide Standard and Protocol for Testing Microbiological water purifiers", 1987 the disclosure of which is herein incorporated by reference to the extent not inconsistent with the present disclosure).

There is an ongoing need to reduce extractables associated with anti-microbial media. There also exists a need to reduce the use of excess materials in forming anti-microbial media.

SUMMARY

Methods of treating filter media with an anti-microbial agent are provided. Methods of use are also provided. In a first aspect, methods for treating filter media with an anti-microbial agent comprise providing a base material of an inorganic component in a processing tank; preparing an anti-microbial component from a mixture; mixing the anti-microbial component with the base material to form a coated base material; maintaining a ratio of the mixture to the base material such that the coated base material is below its compaction point; and drying the coated base material; wherein a covalent bond is formed between the antimicrobial component and the base material by activating the coated base material. In an embodiment, a surface tension of the anti-microbial component is less than a surface tension of the base material. In another embodiment, the step of maintaining the ratio includes adding the mixture in a first amount to achieve the coated base material being above its compaction point, calculating a second amount of the mixture that is in the range of 50-99% by weight of the first amount, repeating the steps of providing the base material and preparing the anti-microbial component, and further mixing the second amount of the mixture with the base material and observing whether the coated base material is at, below, or above its compaction point. Another embodiment provides that the second amount is in the range of 80-99% by weight of the first amount. Other embodiments provide that the step of maintaining the ratio is repeated until the coated base material is below its compaction point.

In detailed embodiments, the anti-microbial component comprises a quaternary ammonium salt containing an epoxide group; and the covalent bond is formed directly between the quaternary ammonium cation and the inorganic component. Another detailed embodiment provides that the quaternary ammonium salt containing the epoxide group has the formula according to I:

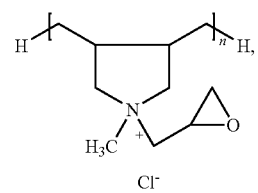

wherein n is in the range of 3 to 250 (or in other embodiments, n is in the range of 5 to 24).

In an embodiment, the mixture for preparing the anti-microbial component comprises poly(methyldiallylamine epichlorohydrin), deionized water, and sodium hydroxide. In other embodiments, the method further comprises adjusting the anti-microbial component to a pH in the range of 8 to 13. In still other embodiments, the mixing step comprises agitating the base material in the processing tank substantially simultaneously with spraying the anti-microbial component into the processing tank to form a coated base material.

A further aspect provides methods for treating filter media with an anti-microbial component, that comprise providing a base material of diatomaceous earth in a processing tank; preparing an anti-microbial component from a mixture comprising a quaternary ammonium salt containing a hydroxyl group, a liquid carrier, and an activating agent, thereby forming an activated quaternary ammonium salt containing an epoxy group; agitating the base material in the processing tank substantially simultaneously with spraying the anti-microbial component into the processing tank to form a coated base material; maintaining a ratio of the mixture to the base material such that the coated base material is below its compaction point; and drying the coated base material under a vacuum; wherein a covalent bond is formed between the activated quaternary ammonium salt containing the epoxide group and the diatomaceous earth. In one or more embodiments, a surface tension of the anti-microbial component is less than a surface tension of the base material.

Detailed embodiments provide that the step of maintaining the ratio includes adding the mixture in a first amount to achieve the coated base material being above its compaction point, calculating a second amount of the mixture that is in the range of 80-99% by weight of the first amount, repeating the steps of providing the base material and preparing the anti-microbial component, and further mixing the second amount of the anti-microbial component with the base material and observing whether the coated base material is at, below, or above its compaction point. The step of maintaining the ratio can be repeated until the coated base material is below its compaction point.

In a detailed embodiment, the ratio is in the range of 0.7:1 to 1.8:1 by weight. One or more embodiments provide that the ratio is 1.5 by weight.

In an embodiment, the diatomaceous earth has a BET surface area in the range of 1 to 2 m²/g and the anti-microbial component comprises the quaternary ammonium salt containing the epoxide group in an amount in the range of 3-10% by weight of the anti-microbial component. The quaternary ammonium salt containing the epoxide group can have the formula according to I wherein n is in the range of 3 to 250 (on in other embodiments, n is in the range of 5 to 24). Further embodiments provide that the coated base material is not washed prior to use in a filter system.

Further aspects provide methods of treating water comprising providing a base material of an inorganic component in a processing tank; preparing an anti-microbial component from a mixture; mixing the anti-microbial component with the base material to form a coated base material; maintaining a ratio of the mixture to the base material such that the coated base material is below its compaction point; drying the coated base material, wherein a covalent bond is formed between the antimicrobial component and the base material by activating the coated base material; forming a filter element from the activated coated base material; and passing water through the filter element.

In another aspect, a method for treating filter media with a functional agent comprises providing a base material of an inorganic component in a processing tank; preparing an anti-microbial component from a mixture; agitating the base material in the processing tank substantially simultaneously with spraying the anti-microbial component into the processing tank to form a coated base material; drying the coated base material; and forming a covalent bond between the anti-microbial component and the base material.

In other embodiments, the method further comprises forming an average particle size of less than 100 microns. A detailed embodiment provides that the average particle size is in the range of 20 to 60 microns.

One embodiment provides that the agitating step is performed by a blender having a paddle, a plow, a ribbon, a helical screw, a rotary drum, a V-blender, or combinations thereof. Another embodiment provides that the agitating step is performed by adding a fluidizing gas to the processing tank to form a fluidized bed of the base material.

In other embodiments, the drying step includes applying a vacuum. Certain embodiments provide that the mixture for preparing the anti-microbial component comprises poly(methyldiallylamine epichlorohydrin), deionized water, and sodium hydroxide. In further embodiments, the method further comprises adjusting the mixture for preparing the anti-microbial component to a pH in the range of 8-13.

In another aspect, a method for treating filter media with an antimicrobial component comprises providing a base material of diatomaceous earth in a processing tank; preparing an anti-microbial component from a mixture comprising a quaternary ammonium salt containing a hydroxyl group, a carrier, and a buffering agent, thereby forming an activated quaternary ammonium salt containing an epoxide group; agitating the base material in the processing tank substantially simultaneously with spraying the anti-microbial component into the processing tank to form a coated base material; drying the coated base material under a vacuum; and forming a covalent bond between the quaternary ammonium cation and the diatomaceous earth. In a detailed embodiment, the activated quaternary ammonium salt containing the epoxide group has the formula according to I, wherein n is in the range of 3 to 250 (or in other embodiments, n is in the range of 5 to 24). A detailed embodiment provides that an average particle size is in the range of 20 to 60 microns. Other embodiments provide that during the agitating and spraying step, the processing tank is heated. In one or more embodiments, the base material achieves a temperature in the range of 40 to 75° C.

In an embodiment, the method further comprises maintaining a ratio of the anti-microbial component to the base material such that the coated base material is below its compaction point. In another embodiment, the drying step occurs substantially simultaneously with the agitating and spraying step.

A further aspect provides a method of treating water comprising: providing a base material of an inorganic component in a processing tank; preparing an anti-microbial component from a mixture; agitating the base material in the processing tank substantially simultaneously with spraying the anti-microbial component into the processing tank to form a coated base material; drying the coated base material; and forming a covalent bond between the anti-microbial component and the base material to form a treated filter media; forming a filter element from the treated filter media; and passing water through the filter element.

Before describing several exemplary embodiments of the invention, it is to be understood that the invention is not limited to the details of construction or process steps set forth in the following description. The invention is capable of other embodiments and of being practiced or being carried out in various ways.

DETAILED DESCRIPTION

Provided are methods of modifying solid porous particles with functional agents to provide anti-microbial media. The purpose of treating such solids with functional agents is to impart such solids with special functions. For example, a solid can be functionalized to offer antimicrobial properties or it can be treated to offer charge capacity.

In certain aspects, methods are provided such that a functional coating material reacts with a substrate material to form a covalent bond, excess amounts of coating material is minimized, and/or the process of coating, surface reaction, and drying are conducted in the same reactor with minimal steps. In this way, the amount of functional coating solutions to the solid particles is maximized but without substantial excess so as to avoid extractables when fluid is flowing through the functionalized solid particles. This leads to reduced costs for raw materials and improved yields.

In one or more embodiments, methods are provided where small solid particles in micron range are coated in a controlled manner so that there is minimal amount of excess material that is not used for coating, and such coating material forms a covalent bond with the substrate after an activation step such as by drying/heating. Methods of making anti-microbial filter media include agitating an inorganic base material in a processing tank substantially simultaneously with spraying the anti-microbial component into the processing tank to form a coated base material.

In another aspect, a liquid to solid ratio can be used to calculate the amount of anti-microbial solution to be used in spray-coating. This is generally balanced with spraying time and vacuum time to keep the material below its compaction point. If the liquid/solid ratio at any point in the mixing cycle exceeds the compaction point of the material, the mixture will become extremely sticky and dry onto the walls of the process chamber, resulting in poor yields.

The following define specific terms, as they are understood to be used in the present disclosure.

Reference to "quaternary ammonium salt" means salts of quaternary ammonium cations with an anion. Quaternary ammonium cations, also known as quats, are positively charged polyatomic ions of the structure NR4+ with R being alkyl groups. Unlike the ammonium ion NH4+ itself and primary, secondary, or tertiary ammonium cations, the quaternary ammonium cations are permanently charged, independent of the pH of their solution. One exemplary quaternary ammonium salt containing an epoxide group is represented by Formula I, below. Note that for stability purposes, the quaternary ammonium salt is shipped in hydroxyl format, and that the epoxide group is expressed once an activating agent, such as a caustic material, is applied.

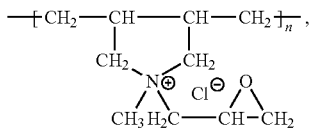

where n is between 3 and 250 (in other embodiments n is in the range of 5 to 24).

The term "particles having an irregular, convoluted surface" refers to particles of unique morphology as set forth in U.S. Pat. No. 7,112,272 (Hughes et al.), incorporated herein by reference in its entirety, which, when compared to particles of substantially spherical shape, show higher surface areas and lower bulk density.

"Fluid filter media" refers to the component(s) of a filtration or separation article that perform an active role in removal of contaminants by virtue of their physical properties or surface chemical properties. The media is typically a particle or combination of particles, or fibers, that have an active role and mechanism in mechanical, chemical reactive, chemical adsorptive electrochemical adsorptive, or chelation (and other filtration/separation mechanisms known in the art). Representative fluid filter media include, but are not limited to activated carbon (AC), diatomaceous earth (DE), powders of polyethylene, fibers of polyethylene and polypropylene, and a lead adsorption component such as titanium silicate (ATS, Engelhard Corp, Iselin, N.J.). Both AC and DE are active media and are major fluid filtration components, as they allow fluids, such as, for example, water to flow through and mechanically separate and/or adsorb undesired species present in influent fluid, such as, for example, water used for drinking purposes, from being present in the effluent fluid stream by at least one or more of the following mechanisms: mechanical sieving, adsorption and charge interactions.

A wide variety of methods and numerous resources are used to supply DE, resulting in diversity in both physical and chemical characteristics. DE is a naturally occurring material, composed of skeletal remains of single-celled plants called diatoms. In the diatoms' lifetimes, the diatoms abstract silica and other minerals from water, and when the diatoms die, only the diatoms skeleton shapes remain. Since DE has a mixture of minute particles of different size, shape and structure, it has been used for many years as a filter media or as a filter aid. The composition of un-processed DE is mostly silica, with some alumina, calcium oxide, iron oxide, titania, etc. Despite its compositional complexity, the surface of DE is covered with hydroxyl groups when in a moisturized environment. The present disclosure describes, among other features, the use of such surface hydroxyl groups to react with charged antimicrobial species so as to charge modify the surface to process antimicrobial ability. It is believed that activated carbon, polymers, ceramics, and transition metals once treated, if necessary, to generate surface hydroxyl groups, may also be reacted in this way to generate antimicrobial activity.

A commercially available un-processed DE is sold under the tradename Celite 501. DE sold under the tradenames Celpure S100 and S300 (available from Advanced Minerals of Santa Barbara, Calif.) are pre-processed to remove metal content and very fine micro-sized particles.

"Fiber" is a particle having an aspect ratio greater than approximately 2:1 (length to width).

"UHMW PE" or "UHMWPE" refers to ultra high molecular weight polyethylene.

"Point-welded" refers to the binding mechanism of the surface of one object to another object at a discrete point. In this application, point-welded is used to describe the bonding relationship between a binder particle such as UHMW-PE to a neighbor particle; the neighboring particle could be another binder, or an active media particle, or a structural member.

"Fail-safe mechanism" means a mechanism that ensures that the final filter maintains its contamination-reduction capability until the end of the design life of the final filter.

"Antimicrobial filter" means a filter that reduces the concentration of microorganisms (including viruses, bacteria, and cyst) in a fluid.

"Adsorption" means the ability of certain solids to preferentially concentrate specific substances from a solution onto its surface, for example, intermolecular forces of attraction between solid and substance adsorbed (Vander Waals attraction).

"Total organic carbon (TOC)" means the amount of carbon covalently bonded in organic molecules. Polyanionic acids like humic and tannic acids are sources of TOC.

Reference to "impulse filling" means that a force is applied to the mold, causing a discrete, substantially vertical displacement that induces movement of at least a portion of the particles in the mold, causing the particles to assume a compact orientation in the mold. This includes indirect methods such as hammer blows to a table to which the molds are clamped and impacts to the table from a pneumatic cylinder, and any suitable direct methods that displace the molds with a series of jarring motions. In some embodiments, the impulse filling comprises a series of discrete displacements (i.e., impulses) applied to the mold. Impulse filling differs from vibration in that there is a period of non-movement or of little movement between the displacements. The period between displacements is typically at least 0.5 (in some embodiments, at least 1, 2, 3, 5, or even at least 10) seconds. The displacement applied to the mold has a vertical component. In some preferred embodiments, the vertical component (as opposed to the horizontal component) accounts for a majority (in some embodiments, a substantial majority (>75%), or even nearly all (>90%)) of the molds movement.

The term "compaction point" refers to a physical condition of a liquid/solid mixture that generally relates to the behavior of the solid particles of the mixture in the presence of the liquid. Below (or before) the compaction point, the mixture will dry to a fluffy powder. Above (or past) the compaction point, the mixture will dry to a solid mass.

The term "spray coating" or "spraying" means that a solution is distributed under pressure and through a nozzle to form fine droplets and land on a substrate.

Reference to "functional agent" means any chemical species that has reactive functional groups and has a potential to react with other species chemically to form a stable bond, such as a covalent bond.

"Surface tension of liquid" means a property of liquids arising from unbalanced molecular cohesive forces at or near the surface, as a result of which the surface tends to contract and to minimize the area of the surface. It can be quantified as the force acting normal to the interface per unit length of the film at equilibrium which also equals the surface energy, the energy required to increase the surface area of the liquid by a unit amount.

"Surface tension of solid" can be considered from three aspects: (1) An atom in the free surface has no neighbors on one side. Since bond energies are negative, its energy is higher than interior atoms by the missing share of bond energy; (2) chemical bonds of surface atoms are asymmetrically directed toward the interior of the material, attracting the surface atoms inward and causing surface tension; and (3) energy required to create a free surface (e.g., by fracture of the material) is reflected in the surface energy.

"Surface wetting" occurs when a solid contacts with a liquid, and when the observed contact angle is zero or so close to zero that the liquid spreads over the solid easily.

Incipient Wetness

The problem of excessive extractables was solved by controlling the amount of surface-modifying solution applied to the surface of a substrate. This was done by first assuming diatomaceous earth particles are porous and conducting incipient wetness coating of surface-modifying solution to the particles. This was done by adding solution to particles slowly while agitating the particles continuously so that the added solution can be spread over the surface of the particles. Generally, this strategy worked only when the solution has lower surface tension than the surface of the substrate so that the solution can wet the surface completely. Since diatomaceous earth is not truly porous, the added solution generally does not go to pores of the particle but spread over the entire surface of the particle. The following table shows the BET surface area of different grades of diatomaceous earth particles before and after surface modification.

| Sample | Modified (Y/N) | Surface Area (m²/g) |
| --- | --- | --- |
| Celite 501 | N | 2.57 |
| Celite 507 | N | 8.70 |
| Celite 545 | N | 1.51 |
| Celite Std. Super Cell | N | 4.91 |
| Celpure 25 | N | 7.96 |
| Celpure 65 | N | 11.65 |
| Celpure 100 | N | 6.28 |
| Celpure 300 | N | 5.29 |
| Celpure 1000 | N | 1.65 |
| Celite 501 as the substrate | Y | 2.43 |
| Celpure 65 as the substrate | Y | 11.61 |

The concentration of the surface modifying solution was optimized so that it was not too viscous, or too concentrated as to precipitate. An exemplary concentration is, but is not limited to, 1 to 20%, and more specifically between 3 to 10%. The optimized concentration was such that the extractable is minimal and the modification is maximal. In an example of charge modifying S-1000 surface with SolfixE solution, the concentration of SolfixE was about 5%, and the weight ratio of solution to substrate was about 0.7 to 1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

While the specific examples and details of the present disclosure relates to microbial reduction in water, it is believed that the technical principles and the specific chemical concepts discussed herein will most likely apply to microbial reduction in the gas phase as well. Thus, whenever the term fluid is used in the present disclosure, it is understood to mean fluid in the conventional sense including liquids, such as for example, water and gas, such as for example, air.

EXAMPLES

Example 1

Modification of DE with poly(methyldiallylamine epichlorohydrin) in the absence of a linker was accomplished as follows. An aqueous solution containing a total of 250 mL was prepared by adding: (i) 62.5 g of poly(methyldiallylamine epichlorohydrin) (available from Ciba Specialty Chemicals under the trade name SolfixE; 20% solids by weight), (ii) 62.5 g 5N sodium hydroxide (NaOH) and (iii) sufficient DI water to bring the total volume to 250 mL. One kilogram of DE (sold under the trade name Celite 501 available from World Minerals of Santa Barbara, Calif.) was placed into a one gallon glass jar. The solution of SolfixE was added in 50 mL aliquots with vigorous shaking, and placed on a roller jar mill for 30 minutes after addition of each 50 mL aliquot. After final addition of the 250 mL SolfixE solution, the one gallon container was allowed to mix on the roller jar mill for 1 hour. The resulting fluffy light mixture was then removed from the one gallon jar and placed onto a glass baking dish. The baking dish was then placed in a convection oven at 110° C. overnight. The dry treated DE product was then washed three times with 0.33 gallons of DI water, vacuum filtered through a Buchner funnel (with #415 filter paper) and dried in a convection oven at 110° C. overnight. The ensuing treated DE contained less than 1-3% water by weight.

Example 2A

Modification of the surface of a high purity/pre-processed DE with poly(methyldiallylamine epichlorohydrin) in the absence of a linker was accomplished as follows. Twenty-five kilograms of high purity/pre-processed DE (sold under the trade name Celpure S1000) was placed into a vessel equipped with a plow and a chopper (Model FM-130; available from Littleford Day Inc.) for agitation. A coating solution was prepared by mixing 9.4 kg poly(methyldiallylamine epichlorohydrin) (available from Ciba Specialty Chemicals under the trade name SolfixE) (20% solids), 2.3 kg 5N NaOH, and 25.8 kg of DI water (including the DI water used in making the 5N NaOH solution). The coating solution was sprayed into the vessel while the S1000 DE was agitated. At the same time, the vessel was steam-heated (steam temperature 152±4° C.) to maintain the S1000 DE temperature at about 55° C. under a vacuum of 26±1 inch Hg. After all of the coating solution was sprayed onto the S1000 DE, the steam was maintained until the temperature of the treated S1000 DE was brought up to about 85° C. The heating steam was then terminated and the material was allowed to cool to room temperature.

Extractables were measured using the metanil yellow capacity test. A one liter aqueous solution containing 8 ppm metanil yellow (available from Sigma-Aldrich, Milwaukee, Wis.) buffered at pH=7.0 was prepared. This solution was recirculated, using a persistalitic pump, through a 47 mm cylindrical housing packed with 934AH glass filter material and 0.1 g of the material to be tested for metanil yellow retention. The initial ($Abs_{(init)}$) and final ($Abs_{(final)}$) visible absorbances (at wavelength=430 nm) were measured using a UV-Visible spectrophotometer (LKB Ultrospec II, available from American Instrument Exchange, Haverhill, Mass.; with a 1.0 cm disposable plastic cell). The capacity (mg/g) was calculated as: Capacity=[$Abs_{(init)}$–$Abs_{(final)}$/$Abs_{(init)}$]*8 ppm/wt of test material.

The surface-modified DE prepared according to Example 2A had reduced extractables compared to the prior art method, both after an initial rinse and after multiple wash steps. Moreover, the method of Example 2A has fewer process steps than that of the prior art method.

The chemical stabilities of the surface-modified DE of Example 2A at a pH of 5 and a pH of 9 were measured by the associated charge capacity and the amount of SolfixE (measured in the form of nitrogen) that could be released to the surrounding water. The pH studies were conducting using the following method. Seventy-five grams (75 g) of the surface modified DE to be tested was placed into each of 18 quart glass jars. To each jar was added 750 mL of tap water. Nine (9) of the mixtures in the jars were adjusted to pH=5.0 using sulfuric acid ($H_2SO_4$) and nine of the mixtures in the quart glass jars were adjusted to pH=9.0 using sodium hydroxide (NaOH). Two blank samples were run containing only pH adjusted DI water. Each sample was prepared by vacuum filtration through a #425 filter paper on a Buchner funnel, and further filtered through a 0.2 micron Zetapor™ nylon membrane (available from CUNO, Inc, Meriden Conn.). Stored samples were shaken daily and pH was monitored and adjusted weekly during the duration of the testing. The water was sampled at 20 minutes, 72 hours, 1 week, 2 weeks, 3 weeks 1 month, 2 months, 4 months and 6 months. The results for pH of 5 are provided in Table 1 and for pH of 9 are provided in Table 2, where TKN is the total Kjeldahl nitrogen in the water, and QAE is total quaternary nitrogen in the water. Neither the TKN nor the QAE values change appreciably over the test timeframe of two months, showing that the surface-modified DE was stable over that timeframe.

TABLE 1

| Sample: pH = 5 | Metanil-Yellow (mg/g) | TKN (ppm) | QAE (ppm) |
| --- | --- | --- | --- |
| DI Water Blank | — | ND | ND |
| 20 minutes | 7 | 1.8 | ND |
| 72 hours | 7.3 | 1.9 | ND |
| 1 week | 8.1 | 1.6 | ND |
| 2 weeks | 6.3 | 2.0 | ND |
| 3 weeks | 4.2 | 1.6 | ND |
| 1 month | 5.6 | 1.3 | ND |
| 2 months | 3.5 | 1.7 | ND |
| 4 months | 6.3 | 1.3 | ND |
| 6 months | 12.4 | 1.3 | ND |

TABLE 2

| Sample: pH = 9 | Metanil-Yellow (mg/g) | TKN (ppm) | QAE (ppm) |
| --- | --- | --- | --- |
| DI Water Blank | — | ND | ND |
| 20 minutes | 11 | 1.7 | ND |
| 72 hours | 14 | 1.8 | ND |
| 1 week | 14.3 | 1.8 | ND |
| 2 weeks | 5.2 | 2.1 | ND |
| 3 weeks | 3.7 | 2.1 | ND |
| 1 month | 8.4 | 1.9 | ND |
| 2 months | 3.2 | 1.7 | ND |
| 4 months | 7.3 | 2.0 | <0.30 |
| 6 months | 9.2 | 1.8 | ND |

"ND" = no analyte detected for the sample

Particle size of DE made according to Example 2 ranges from about 20 to about 60 microns, depending on whether agglomeration occurs. Particle size is a function of agglomeration and can be adjusted as desired via manipulation of process parameters such as spray time/nozzle selection/plow speeds/etc.

Example 2B

Modification of the surface of a high purity/pre-processed DE with poly(methyldiallylamine epichlorohydrin) in the absence of a linker was accomplished as follows. In this example, the relative amounts of DE and poly(methyldiallylamine epichlorohydrin) solution were maintained to keep the mixture of these components below its compaction point. In this method, the DE is surface modified using an amount of charge modification resin needed to effect a uniform modification of the surfaces of the DE particles, without excessive resin that would otherwise result in an undesirable initial water extractable species from the formed zone of the present invention. The result is a highly charged cationic surface modified separation media (active media).

Fifty grams of untreated and fully dried (to less than 1-3 weight % water) high purity DE (S1000) was added slowly to 45 grams of an aqueous solution having about 5.5% by weight of poly(methyldiallylamine epichlorohydrin) (SolfixE). The pH was adjusted to about 11 with NaOH. The addition was slow while S1000 was under constant agitation by tumbling the container tilted at an angle for easy dispensing and without the spilling of the content. Optionally, the container could be a closed system to eliminate moisture loss while agitation.

After the addition was completed, the container was further agitated to ensure a uniform liquid distribution among particles. The container was heated to about 100 to 120° C. to complete the reaction. The total nitrogen content due to SolfixE extracted with water at ambient temperature for 24 hours was less than 2.5 ppm. In certain processes, use of excess SolfixE, not in accordance with staying below the compaction point, normally results in having more than 25 ppm total nitrogen extractable; that is 10 times more extractables as compared with maintaining the compaction point.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

While the articles, apparatus and methods for making the articles contained herein constitute preferred embodiments of the disclosure, it is to be understood that the disclosure is not limited to these precise articles, apparatus and methods, and that changes may be made therein without departing from the scope of the disclosure which is defined in the appended claims.

What is claimed is:

1. A method for treating filter media with an anti-microbial agent, the method comprising:
    providing a base material of an inorganic component in a processing tank;
    preparing an anti-microbial component from a mixture;
    admixing the anti-microbial component with the base material to form a coated base material;
    maintaining a ratio of the mixture to the base material such that the coated base material is below its compaction point; and
    drying the coated base material;
    wherein a covalent bond is formed between the antimicrobial component and the base material by activating the coated base material.

2. The method of claim 1, wherein a surface tension of the anti-microbial component is less than a surface tension of the base material.

3. The method of claim 1, wherein the anti-microbial component comprises a quaternary ammonium salt containing an epoxide group; and the covalent bond is formed directly between the quaternary ammonium cation and the inorganic component.

4. The method of claim 3, wherein the quaternary ammonium salt containing the epoxide group has the formula according to I:

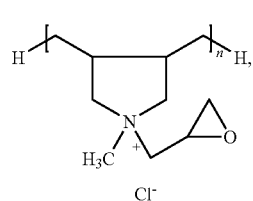

wherein n is in the range of 3 to 250.

5. The method of claim 4, wherein n is in the range of 5 to 24.

6. The method of claim 1, wherein the mixture for preparing the anti-microbial component comprises poly(methyldiallylamine epichlorohydrin), deionized water, and sodium hydroxide.

7. The method of claim 1, further comprising adjusting the anti-microbial component to a pH in the range of 8 to 13.

8. The method of claim 1, wherein the admixing step comprises agitating the base material in the processing tank substantially simultaneously with spraying the anti-microbial component into the processing tank to form a coated base material.

9. A method of treating water comprising:
    providing a base material of an inorganic component in a processing tank;
    preparing an anti-microbial component from a mixture;
    mixing the anti-microbial component with the base material to form a coated base material;
    maintaining a ratio of the mixture to the base material such that the coated base material is below its compaction point;
    drying the coated base material, wherein a covalent bond between the antimicrobial component and the base material by activating the coated base material;
    forming a filter element from the activated coated base material; and
    passing water through the filter element.

* * * * *

UNITED STATES PATENT AND TRADEMARK OFFICE
CERTIFICATE OF CORRECTION

| | | |
|---|---|---|
| PATENT NO. | : 8,123,959 B2 | Page 1 of 1 |
| APPLICATION NO. | : 12/277665 | |
| DATED | : February 28, 2012 | |
| INVENTOR(S) | : Eshan B Yeh | |

It is certified that error appears in the above-identified patent and that said Letters Patent is hereby corrected as shown below:

Column 6
Line 1, delete "S100" and insert -- S1000 --.

Signed and Sealed this
Fourth Day of September, 2012

David J. Kappos
*Director of the United States Patent and Trademark Office*